United States Patent [19]

Callahan et al.

[11] 3,933,751

[45] Jan. 20, 1976

[54] PROMOTED CATALYSTS FOR THE OXIDATION OF OLEFINS

[75] Inventors: James L. Callahan, Bedford Heights; Robert K. Grasselli, Cleveland; Warren R. Knipple, Bedford, all of Ohio

[73] Assignee: The Standard Oil Company, Cleveland, Ohio

[22] Filed: May 7, 1971

[21] Appl. No.: 141,389

Related U.S. Application Data

[63] Continuation-in-part of Ser. No. 638,639, May 15, 1967, abandoned, which is a continuation-in-part of Ser. No. 604,118, Dec. 23, 1966, Pat. No. 3,431,292, which is a continuation-in-part of Ser. No. 311,657, Sept. 26, 1963, Pat. No. 3,328,315.

[52] U.S. Cl. ........... 260/604 R; 252/456; 252/455 R
[51] Int. Cl. ............................................. C07c 45/04
[58] Field of Search ................................. 260/604 R

[56] References Cited
UNITED STATES PATENTS

| | | | |
|---|---|---|---|
| 3,197,419 | 7/1965 | Callahan et al. | 260/604 R |
| 3,198,750 | 8/1965 | Callahan et al. | 260/604 R |
| 3,236,782 | 2/1966 | Koch | 260/604 R |
| 3,313,856 | 4/1967 | Phielix et al. | 260/604 R |
| 3,328,315 | 6/1967 | Callahan et al. | 260/604 R |
| 3,338,952 | 8/1967 | Callahan et al. | 260/604 R |

FOREIGN PATENTS OR APPLICATIONS

| | | | |
|---|---|---|---|
| 991,085 | 5/1965 | United Kingdom | 260/604 R |
| 895,183 | 5/1962 | United Kingdom | 260/604 X |
| 864,666 | 4/1961 | United Kingdom | 260/604 R |

OTHER PUBLICATIONS

Tsutsumi et al., Chemical Abstracts, Vol. 52, Col. 12896, 1958.
Union Chimique, Chem. Abst. Vol. 58, Col. 7413, April 1963.

*Primary Examiner*—Howard T. Mars
*Assistant Examiner*—R. H. Liles
*Attorney, Agent, or Firm*—Herbert D. Knudsen

[57] ABSTRACT

Olefinic aldehydes such as acrolein are produced by the oxidation of an olefin such as propylene in the presence of an antimony oxide-uranium oxide catalyst containing at least one of a number of specified promoter elements.

10 Claims, No Drawings

PROMOTED CATALYSTS FOR THE OXIDATION OF OLEFINS

This is a continuation-in-part of our co-pending application Ser. No. 638,639 filed May 15, 1967 now abandoned, which in turn is a continuation-in-part of our application Ser. No. 604,118 filed Dec. 23, 1966 now U.S. Pat. No. 3,431,292, which in turn is a continuation-in-part of our application Ser. No. 311,657 filed Sept. 26, 1963 now U.S. Pat. No. 3,328,315.

This invention relates to promoted oxidation catalysts containing the elements of antimony and uranium and more particularly pertains to antimony-uranium catalysts containing minor amounts of an element or elements selected from Groups IA, IB, IIA, IIB, IIIB, IVA, IVB, VB, VIIB and VIII of the Periodic Table. The catalysts of the present invention are particularly useful in the oxidation of olefins, such as propylene and isobutylene, to oxygenated hydrocarbons, such as acrolein and methacrolein, respectively.

The base antimony-uranium oxide catalyst useful in the present invention is more fully described in U.S. Pat. No. 3,198,750. Attrition resistant catalysts of these types are described more completely in U.S. Pat. No. 3,341,471. The base catalyst consists essentially of the oxides of uranium and antimony. The exact nature of the chemical compound or compounds which compose the catalyst of this invention is not known. The catalyst may be a mixture of antimony oxide or oxides and uranium oxide or oxides. It is also possible that the antimony and uranium are combined with the oxygen to form an antimonate or uranate. X-ray examination of the catalyst has indicated the presence of a structurally common phase of the antimony type, comprised of antimony oxide and some form of uranium oxide. For the purpose of the description of the invention, the base catalyst will simply be referred to as a mixture of antimony and uranium oxides, but this is not to be construed as meaning that the catalyst is composed either in whole or in part of these compounds.

The proportions of antimony and uranium in the base catalyst may vary widely. The Sb:U atomic ratio can range from about 1:50 to about 99:1. However, optimum activity appears to be obtained at Sb:U atomic ratios within the range from 1:1 to 25:1.

It is preferred that the catalyst of this invention be combined with from 10 to 90% by weight of a silica support.

The antimony oxide and uranium oxide can be blended together, or can be formed separately and then blended or formed separately or together in situ. As starting materials for the antimony oxide component, for example, there can be used an antimony oxide, such as antimony trioxide, antimony tetroxide and antimony pentoxide, or mixtures thereof; or a hydrous antimony oxide, metaantimonic acid, orthoantimonic acid or pyroantimonic acid; or a hydrolyzable or decomposable antimony salt, such as antimony halide, for example, antimony trichloride, trifluoride or tribromide; antimony pentachloride and antimony pentafluoride, which is hydrolyzable in water to form the hydrous oxide. Antimony metal can be employed, the hydrous oxide being formed by oxidizing the metal with an oxidizing acid, such as nitric acid.

The uranium oxide component can be provided in the form of uranium oxide or by precipitation in situ from a soluble uranium salt such as the nitrate, acetate, or a halide such as the chloride. Uranium metal can be used as a starting material, and if antimony metal is also employed, the antimony can be converted to the oxide and uranium to the nitrate simultaneously by oxidation in hot nitric acid. A slurry of hydrous antimony oxide formed in situ from the metal in nitric acid also can be combined with a solution of a uranium salt such as uranium nitrate, which is then precipitated in situ as uranium oxide by the addition of ammonium hydroxide. The ammonium nitrate and any other soluble salts are removed by filtration of the resulting slurry or by thermal decomposition.

It will be apparent from the above that uranium tribromide, uranium tetrabromide, uranium trichloride, uranium tetrachloride, uranium pentachloride, uranium hexafluoride, uranium tetraiodide, uranyl nitrate, uranyl sulfate, uranyl chloride, uranyl bromide, uranium trioxide, and uranium peroxide can be employed as the source of the uranium oxide component.

The catalytic activity of the system is enhanced by heating at an elevated temperature. Preferably, the catalyst mixture is dried and heated at a temperature of from about 500° to about 1150°F, preferably at about 700° to 900°F, for from 2 to 24 hours. If activity then is not sufficient, the catalyst can be further heated at a temperature above about 1000°F but below a temperature deleterious to the catalyst at which it is melted or decomposed, preferably from about 1400° to about 1900°F, for from 1 to 48 hours, in the presence of air or oxygen. Usually this limit is not reached before 2000°F and in some cases this temperature can be exceeded.

In general, the higher the activation temperature, the less time required to effect activation. The sufficiency of activation at any given set of conditions is ascertained by a spot test of a sample of the material for catalytic activity. Activation is best carried out in an open chamber, permitting circulation of air or oxygen, so that any oxygen consumed can be replaced.

The antimony oxide-uranium oxide base catalyst composition useful in the invention can be defined by the following empirical formula:

$$Sb_a U_b O_c$$

wherein '$a$' is 1 to 99, '$b$' is 50 to 1, and '$c$' is a number taken to satisfy the average valences of antimony and uranium in the oxidation states in which they exist in the catalyst as defined by the empirical formula above. Thus, the Sb valence may range from 3 to 5 and the U valence from 4 to 6.

OXIDATION OF OLEFINS TO OXYGENATED COMPOUNDS

The reactants used in the oxidation to oxygenated compounds are oxygen and an olefin having only three carbon atoms in a straight chain such as propylene or isobutylene or mixtures thereof.

The olefins may be in admixture with paraffinic hydrocarbons such as ethane, propane, butane and pentane, for example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e. −10 to 100 psig, temperatures in the range of 500° to 1100°F may be advantageously employed. However, the process may be conducted at other pressures, and in the case where superatmospheric pressures, e.g. above 100 psig, are employed, somewhat lower temperatures are possible. In the case where this process is employed to convert propylene to acrolein, a temperature range of 750° to 950°F has been found to be optimum at atmospheric pressure.

While pressures other than atmospheric may be employed, it is generally preferred to operate at or near atmospheric pressure, since the reaction proceeds well at such pressures and the use of expensive high pressure equipment is avoided.

The apparent contact time employed in the process is not critical and it may be selected from a broad operable range which may vary from 0.1 to 50 seconds. The apparent contact time may be defined as the length of time in seconds which the unit volume of gas measured under the conditions of reaction is in contact with the apparent unit volume of the catalyst. It may be calculated, for example, from the apparent volume of the catalyst bed, the average temperature and pressure of the reactor, and the flow rates of the several components of the reaction mixture.

The optimum contact time will, of course, vary depending upon the olefin being treated, but in the case of propylene and isobutylene, the preferred apparent contact time is 0.15 to 15 seconds.

A molar ratio of oxygen to olefin between about 0.5:1 to 5:1 generally gives the most satisfactory results. For the conversion of propylene to acrolein, a preferred ratio of oxygen to olefin is from about 1:1 to about 2:1. The oxygen used in the process may be derived from any source; however, air is the least expensive source of oxygen and is preferred for that reason.

We have also discovered that the addition of water to the reaction mixture has a marked beneficial influence on the course of the reaction in that it improves the conversion and the yields of the desired product. The manner in which water affects the reaction is not fully understood but the theory of this phenomenon is not deemed important in view of the experimental results we have obtained. Accordingly, we prefer to include water in the reaction mixture. Generally, a ratio of olefin to water in the reaction mixture of from 1:0.5 to 1:10 will give very satisfactory results, and a ratio of from 1:0.75 to 1:6 has been found to be optimum when converting propylene to acrolein. The water, of course, will be in the vapor phase during the reaction.

Inert diluents such as nitrogen and carbon dioxide may be present in the reaction mixture.

In general, any apparatus of the type suitable for carrying out oxidation reactions in the vapor phase may be employed in the execution of this process. The process may be conducted either continuously or intermittently. The catalyst bed may be a fixed bed employing a large particulate or pelleted catalyst or, in the alternative, a so-called "fluidized" bed of catalyst may be employed.

The reactor may be brought to the reaction temperature before or after the introduction of the reaction feed mixture. However, in a large scale operation, it is preferred to carry out the process in a continuous manner, and in such a system the recirculation of the unreacted olefin is contemplated.

The promoter element or elements may be added to the base catalyst in amounts ranging from 0.01 to about 20% by weight based on the weight of the promoted base catalyst. Combinations of two or more promoter elements is contemplated to be within the scope of the present invention. The promoters may be incorporated into the base catalyst by co-precipitation or impregnation. Promoter elements are conveniently added in the form of their nitrates or other salts. In any event, the promoter elements, like the antimony and uranium, probably exist in the final active catalyst in the form of their oxides.

Specific elements which are useful promoters in combination with the base catalysts are bismuth, indium, platinum, magnesium, silver, iron, zirconium, copper, thorium, zinc, cadmium, cobalt, nickel, rhenium, barium, lead, arsenic, tungsten, phosphorous, aluminum, cerium, calcium, antimony, cesium, iridium and palladium. Most preferred promoter elements are bismuth, platinum, magnesium, silver, iron, zirconium, copper, thorium, zinc, cobalt, nickel, lead, aresinc, tungsten, phosphorous, aluminum, calcium, antimony and cesium.

The process of the present invention is further illustrated in the following examples wherein the amounts of ingredients are expressed as parts by weight unless otherwise indicated.

EXAMPLE I 90 grams of antimony metal were completely oxidized in 360 mls. of concentrated nitric acid. 81.4 grams of $UO_2(NO_3)_2 \cdot 6H_2O$ and 228 grams of duPont Ludox HS (30% by weight of $SiO_2$ in water) were mixed into the acidic mixture. By addition of concentrated ammonium hydroxide the slurry was brought to a pH of 8. The precipitate was filtered and washed and then divided into four portions. At this point different promoter elements in different amounts ranging from about 1 to 10% by weight based on the weight of the active base catalyst were incorporated into each of these fractions. To the wet filter cake was added a specified quantity of the promoter element nitrate, oxide, sulfate, or chloride dissolved in a minimum amount of water, and the mixture was then blended or mixed together to give a uniform distribution. Each catalyst was then dried at 120°C and calcined at 800°F. Finally, the catalyst was activated at a temperature above 1000°F. This formulation produced a base catalyst of 70% by weight of $USb_{4.6}O_{11.8}$ and 30% by weight of silica.

126 grams of the above-described wet catalyst filter cake and 6.1 g. $Bi(NO_3)_3 \cdot 5H_2O$ were mixed together. The promoted catalyst was dried at 120°C and calcined at 800°F for 24 hours. It was then heat-treated at 1800°F for 8 hours. Dry weight of the promoted catalyst containing 6.36% by weight of bismuth in the active component was 59 grams.

2.7 grams of $In_2(SO_4)_3$ were treated with concentrated $NH_4OH$ and then the resulting material was filtered, washed and mixed with the wet catalyst filter cake described above. The promoted catalyst was dried at 120°C, calcined at 800°F for 24 hours and heat-treated at 1800°F for 8 hours. Dry weight of the promoted catalyst was 59 grams and the promoted catalyst contained 2.89% by weight of In based on the active component.

0.9 gram of $PtCl_4$ (in a 10% aqueous solution) was added to the wet catalyst filter cake. The promoted catalyst was dried at 120°C, calcined at 800°F for 24 hours and heat-treated at 1800°F for 8 hours. Dry weight of the promoted catalyst was 52 grams. The promoted catalyst contained 1.42% by weight of Pt based on the active component of the catalyst.

EXAMPLE II

An attrition resistant catalyst was prepared as follows:

180 grams of antimony metal were completely oxidized in 720 mls. of concentrated $HNO_3$. 162.8 grams of $UO_2(NO_3)_2 \cdot 6H_2O$ were added and the mixture was evaporated almost to dryness. 456.8 grams of duPont HS Ludox (a 30% by weight $SiO_2$ dispersion in water) were added and the mixture was brought to a pH of 8.0 by the addition of $NH_4OH$. The catalyst was filtered and washed with 600 mls. of water in two separate portions. The catalyst was then dried at 120°C, calcined at 800°F for 24 hours and heat-treated at 1725°F for 8 hours. 444 grams of the foregoing catalyst were mixed with 247 grams of Ludox and the resulting product was extruded. The extrudate was dried at 120°C and then heat-treated at 1725°F for 72 hours.

25 grams of the above-described catalyst in the size range which would pass a 35 mesh screen but be retained on an 80 mesh screen, were mixed with a solution of 1.13 grams of $In_2SO_4$ in 10 mls. of water. This mixture was made basic with 5 mls. of 28% $NH_4OH$. It was then filtered and washed with 30 mls. of $H_2O$ in three portions. The promoted catalyst was dried at 120°C, calcined at 800°F for 2 hours and heat-treated at 1725°F for 2 hours.

EXAMPLE III

Propylene:air mixtures were converted to acrolein using promoted catalysts prepared by the procedures given in Examples I and II. The reactor unit was made up of a feed induction system, a molten salt bath furnace, stainless steel microreactor containing 5 mls. of catalyst, microadsorption system and a vapor fractometer. In order to provide a steady feed stream and to maintain constant contact time, low pressure regulators (Moore Products Co., 0 to 50 inches of water) were used in connection with flow meters. The reactor was placed in the salt bath which was maintained at a constant temperature. Connections from the feed induction system to the reactor and from the reactor to the adsorption unit were made with silicone rubber seals.

All gases leaving the reactor were passed through a sintered glass tube into a half normal aqueous HCl solution. An internal standard was incorporated into the HCl solution by adding 5 mls. of methyl ethyl ketone per liter of solution. In order to insure a minimal loss of product, the HCl solution was kept at ice bath temperature.

Separation of the products was accomplished in a Perkin-Elmer Fractometer under the following conditions: Column: a 2-meter length of a quarter-inch stainless steel tubing, 35% polyethylene glycol on 30 or 60 mesh fire brick, 100°C, 68 mls. of helium per minute carrier gas.

The catalyst column in the reactor was 5 mls., the contact time was 3 seconds. The reaction temperature was 880°F. In each case a 6 minute pre-run was conducted followed by a 12 minute run in which product was collected. The molar feed ratio used of propylene to air was 1:10, respectively. The results are given in Table I.

TABLE I

| % Promoter in Catalyst | % Per Pass Conversion of Propylene to Acrolein |
|---|---|
| 2.50 Mg | 57.9 |
| 4.25 Ag | 60.0 |
| Unpromoted | 50.0 |
| 3.51 Zn | 61.4 |
| 3.99 Ni | 56.8 |
| 3.83 Pb | 55.0 |
| 1.52 As | 62.3 |
| 1.55 W | 58.4 |
| 4.28 Co | 54.8 |
| 4.81 Fe | 54.6 |
| 4.08 Ba | 54.4 |
| 5.47 Cu | 53.7 |

EXAMPLE IV

The procedures outlined in Example III were used in the conversion of isobutylene to methacrolein. The reaction temperature was 770°F, contact time was 3.6 seconds, the pre-run lasted 10 minutes and the run itself lasted 15 minutes. The molar feed ratio of isobutylene:air was 1:10, respectively. The results are given in Table II.

TABLE II

| Promoter in Catalyst | Weight % Promoter | % Per Pass Conversion of Isobutylene to Methacrolein |
|---|---|---|
| Fe | 0.56 | 60.6 |
| Cs | 1.87 | 58.8 |
| Mg | 0.49 | 58.2 |
| Zn | 8.29 | 56.5 |
| Bi | 2.87 | 52.9 |
| Pd | 1.90 | 51.2 |
| Unpromoted | — | 47.0 |
| Mg + Cu | 0.36 + 0.95 | 57.5 |
| Bi + Cu | 3.14 + 0.95 | 53.8 |

We claim:
1. The process for the manufacture of unsaturated aldehydes which comprises the step of contacting in the vapor phase, at a temperature in the range of 500° to 1100°F, a mixture of oxygen and an olefin selected from the group consisting of propylene and isobutylene, said mixture having a molar ratio of oxygen to olefin of from about 0.5:1 to about 5:1 with a promoted catalyst composition consisting essentially of a base catalyst, a support and a promoter component, said base catalyst consisting essentially of the oxides of antimony and uranium, the Sb:U atomic ratio being within the range of about 1:50 to 99:1, said support being silica and said promoter component consisting essentially of an oxide of at least one element selected from the group consisting of iron, magnesium, bismuth, copper, zinc, arsenic, and cesium.

2. The process of claim 1 wherein the olefin is propylene.

3. The process of claim 1 wherein the olefin is isobutylene.

4. The process of claim 1 wherein the promoter component is an oxide of zinc.

5. The process of claim 1 wherein the promoter component is an oxide of arsenic.

6. The process of claim 1 wherein the promoter component is an oxide of cesium.

7. The process of claim 1 wherein the promoter component is an oxide of magnesium.

8. The process of claim 1 wherein the promoter component is an oxide of bismuth.

9. The process of claim 1 wherein the promoter component is an oxide of iron.

10. The process of claim 1 wherein the promoter component is the combined oxides of magnesium and copper.

* * * * *